US011339115B2

(12) United States Patent
Wucher et al.

(10) Patent No.: US 11,339,115 B2
(45) Date of Patent: May 24, 2022

(54) INCREASING THE CATALYST SELECTIVITY IN THE CONTINUOUS HYDROGENATION OF NITRO COMPOUNDS BY ADDING AMMONIA

(71) Applicant: BASF SE, Ludwigshafen am Rhein (DE)

(72) Inventors: Barbara Wucher, Ludwigshafen (DE); Thomas Heidemann, Ludwigshafen (DE); Michael Friko, Ludwigshafen (DE); Christian Bechtold, Ludwigshafen (DE)

(73) Assignee: BASF SE (DE)

( * ) Notice: Subject to any disclaimer, the term of this patent is extended or adjusted under 35 U.S.C. 154(b) by 1 day.

(21) Appl. No.: 16/649,885

(22) PCT Filed: Oct. 8, 2018

(86) PCT No.: PCT/EP2018/077238
§ 371 (c)(1),
(2) Date: Mar. 23, 2020

(87) PCT Pub. No.: WO2019/076658
PCT Pub. Date: Apr. 25, 2019

(65) Prior Publication Data
US 2020/0270197 A1    Aug. 27, 2020

(30) Foreign Application Priority Data
Oct. 16, 2017 (EP) .................................... 17196607

(51) Int. Cl.
C07C 209/36 (2006.01)
B01J 21/18 (2006.01)
B01J 23/89 (2006.01)

(52) U.S. Cl.
CPC ............ *C07C 209/36* (2013.01); *B01J 21/18* (2013.01); *B01J 23/892* (2013.01); *B01J 23/8993* (2013.01)

(58) Field of Classification Search
CPC . C07C 209/36; C07C 209/365; C07C 209/32; C07C 209/325; C07C 209/34; B01J 21/18; B01J 23/892; B01J 23/8993
See application file for complete search history.

(56) References Cited

U.S. PATENT DOCUMENTS

| | | | | |
|---|---|---|---|---|
| 2,739,985 A * | 3/1956 | Huber | .................... | C07C 211/46 564/416 |
| 2,823,235 A * | 2/1958 | Penrose | ................. | C07C 209/36 564/423 |
| 3,145,231 A * | 8/1964 | Kosak | ........................... | 564/417 |
| 3,255,248 A * | 6/1966 | Suessenguth | ......... | C07C 211/35 564/314 |
| 3,361,819 A * | 1/1968 | Kosak | ............................ | 564/417 |
| 4,185,036 A * | 1/1980 | Cossaboon | .............. | B01J 23/40 562/458 |
| 4,482,769 A * | 11/1984 | Toseland | ............... | C07C 201/16 568/934 |
| 4,978,792 A * | 12/1990 | Nagata | ................... | C07C 209/36 564/384 |
| 5,120,875 A * | 6/1992 | Birkenstock | ........ | C07C 209/365 564/417 |
| 6,140,539 A * | 10/2000 | Sander | .................... | B01J 35/006 564/421 |
| 6,680,280 B1 * | 1/2004 | Birke | ...................... | B01J 23/755 502/337 |
| 9,505,705 B2 * | 11/2016 | Kubanek | ................... | B01J 37/16 |
| 10,538,478 B2 * | 1/2020 | Lange De Oliveira | ...................... | B01J 23/892 |
| 2004/0073066 A1 * | 4/2004 | Zehner | ................... | C07C 211/50 564/416 |
| 2008/0177111 A1 * | 7/2008 | van Laar | ................ | C07C 209/36 564/423 |
| 2008/0242537 A1 * | 10/2008 | Kubanek | .............. | B01J 23/8953 502/326 |
| 2013/0123540 A1 * | 5/2013 | Goettel | .................. | C07C 209/36 564/423 |
| 2014/0039227 A1 * | 2/2014 | Neto | ...................... | C07C 205/06 568/934 |
| 2015/0073180 A1 * | 3/2015 | Knauf | ................... | C07C 209/36 568/939 |

FOREIGN PATENT DOCUMENTS

| | | |
|---|---|---|
| CN | 103387498 A | 11/2013 |
| CN | 104710316 A | 6/2015 |
| DE | 24 61 615 A1 | 7/1975 |
| DE | 2743610 A1 * | 3/1979 |
| DE | 101 05 277 A1 | 8/2002 |
| DE | 10 2005 041 532 A1 | 3/2007 |
| DE | 10 2008 063 308 B4 | 3/2013 |
| EP | 1 161 297 A1 | 12/2001 |
| EP | 1 165 231 A1 | 1/2002 |
| EP | 1 678 118 B1 | 4/2012 |
| WO | WO 00/35852 A1 | 6/2000 |
| WO | WO 00/51727 A1 | 9/2000 |
| WO | WO 00/51728 A1 | 9/2000 |

(Continued)

OTHER PUBLICATIONS

N.G. Anderson, Practical Process & Research Development (2000) (Year: 2000).*
European Search Report dated Mar. 29, 2018 for EP Patent Application No. 17196607.0, 3 pages.
International Search Report dated Nov. 28, 2018 for PCT Patent Application No. PCT/EP2018/077238, 4 pages.

(Continued)

*Primary Examiner* — Alexander R Pagano
(74) *Attorney, Agent, or Firm* — Faegre Drinker Biddle & Reath LLP

(57) ABSTRACT

The present invention relates to a process for continuous hydrogenation of a nitro compound to the corresponding amine in a liquid reaction mixture comprising the nitro compound in a reaction chamber in the presence of a supported catalyst which comprises as the active component at least one element from groups 7 to 12 of the periodic table of the elements, wherein ammonia is added to the reaction chamber during the hydrogenation.

16 Claims, No Drawings

(56) References Cited

FOREIGN PATENT DOCUMENTS

| WO | WO 03/066571 A1 | 8/2003 | |
|---|---|---|---|
| WO | WO 2008/138784 A1 | 11/2008 | |
| WO | WO 2008/145179 A1 | 12/2008 | |
| WO | WO 2010/125025 A1 | 11/2010 | |
| WO | WO 2014/108351 A1 | 7/2014 | |
| WO | WO-2018069278 A1 * | 4/2018 | ........... C07C 209/36 |

OTHER PUBLICATIONS

U.S. Appl. No. 16/340,593, filed Jan. 1, 2020, US 2019-0233364 A1, Armin Lange De Oliveira et al.
U.S. Appl. No. 16/340,478, filed Apr. 9, 2019, US 2019-0241501 A1, Armin Lange De Oliveira et al.
International Search Report dated Nov. 28, 2018 in PCT/EP2018/077238 filed on Oct. 8, 2018, 3 pages.

* cited by examiner

INCREASING THE CATALYST SELECTIVITY IN THE CONTINUOUS HYDROGENATION OF NITRO COMPOUNDS BY ADDING AMMONIA

The present invention relates to a process for continuous hydrogenation of a nitro compound to the corresponding amine in a liquid reaction mixture comprising the nitro compound in a reaction chamber in the presence of a supported catalyst which comprises as the active component at least one element from groups 7 to 12 of the periodic table of the elements, wherein ammonia is added to the reaction chamber during the hydrogenation.

Processes for continuous hydrogenation of nitro compounds to the corresponding amines are known per se.

A commonly described difficulty in processes for hydrogenation of nitro compounds to the corresponding amines is the release of large amounts of reaction heat and associated potentially high reaction temperatures.

DE 10 2008 063308 B4 describes a process for producing tolylenediamine by hydrogenation of dinitrotoluene where the reaction heat is utilized for obtaining steam which is introduced into a steam network of an industrial plant and may be utilized further. Steam generation necessarily requires reaction temperatures greater than 100° C. The hydrogenation disclosed in DE 10 2008 063308 B4 is performed at a temperature of not less than 180° C.

However, an often described problem of high reaction temperatures during hydrogenation are undesired side reactions which also proceed via local hotspots inside the reactor for example.

WO 2014/108351 A1 describes an apparatus of the loop venturi reactor type for the continuous reaction of liquids with gases, in particular for hydrogenations, oxidations or acetylations, for example for the production of tolylenediamine by hydrogenation of dinitrotoluene. In the case of a large amount of evolved reaction heat local temperature spikes are avoided by modification of the arrangement of the heat transfer tubes of the reactor. Catalysts used are for example activated nickel catalysts according to WO 2008/145179 A1 which are composed of a doped Ni/Al alloy and are not supported. One problem with such Ni/Al alloys is the formation of nickel aluminates, such as takovite or takovite-like compounds. Nickel aluminates are formed in the hydrogenation of nitroaromatics when the Ni/Al catalyst comprises more than 5.5 wt % of Al. They form solids which are deposited on the walls of the reactor and the peripheral apparatuses, such as pumps. This can result in a reduction in the efficiency of heat transfer of the system and even in blockages of the system. One or more metals selected from the group consisting of Mg, Ce, Ti, V, Nb, Cr, W, Mn, Re, Fe, Ru, Co, Rh, Ir, Pt, Cu, Ag, Au and Bi are used to dope the Ni/Al alloy of the activated nickel catalyst from WO 2008/145179 A1 in order to reduce or completely avoid the formation of nickel aluminates such as takovite or takovite-like compounds.

EP 1678118 B1 discloses a process for producing amines by catalytic hydrogenation of the corresponding nitro compounds. In order to combat side reactions which result in the formation of high molecular weight byproducts or in the formation of low boilers the selectivity of the process is improved using a catalyst consisting of platinum and nickel.

DE 10 2005 041532 A1 likewise describes a process for producing amines by catalytic hydrogenation of the corresponding nitro compounds with reduced side reactions and improved selectivity of the process using a catalyst consisting of platinum, nickel and an additional metal.

A further problem with the known processes is that after a prolonged running time of the reaction process, the product yield is reduced on account of the aging of the catalyst. For example impurities in the reactant supplied, or the products of undesired side reactions, can contribute to the aging of the catalyst. The aging of the catalyst may additionally be accelerated by an interruption in the supply of the reactant, for example during a pause in operation.

When a reactor with recycling of matter, a so-called loop reactor, is employed there may be regions in which a complete conversion of the reactant takes place. The aging of the catalyst may be accelerated in these regions since as a result of the complete conversion of the reactant the formation of high-boiling components, such as various amino- and methyl-substituted diphenylamines, hydrazodiphenyls and phenazines, takes place to a greater extent.

Furthermore, an interruption in the supply of nitro compounds while maintaining the reaction conditions (such as temperature, pressure, hydrogen stream and flow in the Loop reactor (circulation stream)) and all other conditions results in formation of high-boiling components, such as various amino- and methyl-substituted diphenylamines, hydrazodiphenyls and phenazines, which can deactivate the catalyst. When the process is resumed by renewed supply of nitro compounds the yield of amines is markedly lower and generally recovers only slowly and incompletely.

It is an object of the present invention in a process for continuous hydrogenation of nitro compounds to the corresponding amines to maintain the activity of the catalyst for longer periods without having to reduce the feed rate of the reactants or the temperature. Furthermore the selectivity of the catalyst should be increased. It is a further object of the present invention to reduce the formation of high-boiling components which result in contamination of the catalyst and in deactivation thereof.

The object is achieved by a process for continuous hydrogenation of a nitro compound to the corresponding amine in a liquid reaction mixture comprising the nitro compound in a reaction chamber in the presence of a supported catalyst which comprises as the active component at least one element from groups 7 to 12 of the periodic table of the elements, wherein ammonia is added to the reaction chamber during the hydrogenation.

It was found that, surprisingly, the addition of ammonia during the hydrogenation significantly increases the product yield of amines. Simultaneously, the formation of high-boiling components during the process is reduced and the lifetime of the catalyst increased. The ammonia is also easily removable from the reaction product, for example by distillative methods.

Surprisingly, the formation of high-boiling components is also reduced when ammonia is present in the reactor prior to an interruption in the supply of nitro compounds. The reaction yield of amines returns to its previous level immediately after resumption of the reaction through supply of nitro compounds.

The process according to the invention for continuous hydrogenation of a nitro compound to the corresponding amine in a liquid reaction mixture comprising the nitro compound in a reaction chamber in the presence of a supported catalyst which comprises as the active component at least one element from groups 7 to 12 of the periodic table of the elements involves ammonia being added to the reaction chamber during the hydrogenation.

Adding ammonia into the reaction space during the hydrogenation is to be understood as meaning that the addition of the ammonia is carried out continuously with the other reactants while the reaction, namely the hydrogenation, takes place and does not include an initial charge of the desired ammonia amount before actual commencement of the reaction; reaction space is to be understood as meaning a space within which the continuous hydrogenation of the nitro compound is carried out.

The active component of the supported catalyst generally comprises at least one element from the group consisting of nickel, platinum, palladium, iron and cobalt.

In a first preferred embodiment the active component of the supported catalyst comprises nickel in the form of nickel crystallites having a bimodal nickel crystallite size distribution and has a nickel content of 60 to 80 wt % based on the total mass of the catalyst and a degree of reduction of at least 70%.

In a second preferred embodiment the active component of the supported catalyst comprises a mixture of nickel and platinum and optionally at least one additional metal. The hydrogenation catalyst of this second preferred embodiment preferably comprises 1 to 5 wt % of platinum, 0.3 to 1.5 wt % of nickel, 0.05 to 1.5 wt % of the at least one additional metal and 94.65 to 97.45 wt % of support material based on the total weight of the catalyst. The at least one additional metal is preferably chromium.

Nitro Compounds

The nitro compounds employed in the process according to the invention are organic compounds having at least one nitro group.

Suitable nitro compounds are for example nitro alcohols and nitroaromatics.

Suitable nitro alcohols are for example tris(hydroxymethyl)nitromethane, 2-nitro-2-methyl-1,3-propanediol, 2-nitro-2-ethyl-1,3-propanediol, 2-nitro-1-butanol and 2-nitro-2-methyl-1-propanol and any desired mixtures of two or more of the recited nitro alcohols. These are hydrogenated to the corresponding aminoalcohols.

In a preferred embodiment the nitro compound for hydrogenation is a nitroaromatic. Suitable nitroaromatics are mononitroaromatics, dinitroaromatics and polynitroaromatics. Polynitroaromatics in the context of the invention are nitroaromatics having at least three nitro groups. Preference is given to hydrogenating mononitroaromatics or dinitroaromatics, particularly preferably dinitroaromatics.

The mononitroaromatics used generally have 6 to 18 carbon atoms. Suitable mononitroaromatics are mononitrotoluenes and the halogen derivatives thereof and also mononitrobenzenes and the halogen derivatives thereof, for example nitrobenzene, o-nitrotoluene, m-nitrotoluene, p-nitrotoluene, mononitroxylenes, such as 1,2-dimethyl-3-nitrobenzene, 1,2-dimethyl-4-nitrobenzene, 1,4-dimethyl-2-nitrobenzene, 1,3-dimethyl-2-nitrobenzene, 2,4-dimethyl-1-nitrobenzene and 1,3-dimethyl-5-nitrobenzene, mononitronaphthalenes, such as 1-nitronaphthalene and 2-nitronaphthalene, chloronitrobenzenes, such as o-chloronitrobenzene, m-chloronitrobenzene, p-chloronitrobenzene, or 1,2-dichloro-4-nitrobenzene, 1,4-dichloro-2-nitrobenzene, 2,4-dichloro-1-nitrobenzene and 1,2-dichloro-3-nitrobenzene, chloronitrotoluenes, such as 4-chloro-2-nitrotoluene, 4-chloro-3-nitrotoluene, 2-chloro-4-nitrotoluene and 2-chloro-6-nitrotoluene and nitroanilines, such as o-nitroaniline, m-nitroaniline or p-nitroaniline.

Preferred mononitroaromatics are mononitrobenzenes, halogenated mononitrobenzenes and mononitrotoluenes, particular preference being given to nitrobenzene, o-nitrotoluene, m-nitrotoluene, p-nitrotoluene, 1,2-dimethyl-3-nitrobenzene, 1,2-dimethyl-4-nitrobenzene, 1,4-dimethyl-2-nitrobenzene, 1,3-dimethyl-2-nitrobenzene, 2,4-dimethyl-1-nitrobenzene, 1,2-dichloro-4-nitrobenzene, 1,4-dichloro-2-nitrobenzene, 2,4-dichloro-1-nitrobenzene or 1,2-dichloro-3-nitrobenzene, very particular preference being given to o-nitrotoluene, m-nitrotoluene and p-nitrotoluene.

The dinitroaromatics used generally have 6 to 18 carbon atoms. Suitable dinitroaromatics are dinitrotoluenes and the halides thereof, dinitrobenzenes and the halides thereof and also dinitronaphthalenes. Compounds that may be used include for example 1,3-dinitrobenzene, 2,4-dinitrotoluene, 2,6-dinitrotoluene, dinitroxylenes, such as 2,4-dinitro-m-xylene, 3,5-dinitro-o-xylene, 4,5-dinitro-o-xylene or 4,6-dinitro-m-xylene, dinitronaphthalenes, such as 1,5-dinitronaphthalene or 1,8-dinitronaphthalene, or chloronitrobenzenes, such as 2-chloro-1,3-dinitrobenzene or 1-chloro-2,4-dinitrobenzene.

Preferred nitroaromatics are dinitrobenzenes, halogenated dinitrobenzenes, dinitronaphthalenes and dinitrotoluenes, particularly preferably m-dinitrobenzene, 1,5-dinitronaphthalene, 1,3-dinitrobenzene, 2,4-dinitrotoluene, 2,6-dinitrotoluene, 2-chloro-1,3-dinitrobenzene and 1-chloro-2,4-dinitrobenzene and very particularly preferably m-dinitrobenzene, 1,5-dinitronaphthalene, 2,4-dinitrotoluene and 2,6-dinitrotoluene.

The polynitroaromatics used generally have 6 to 18 carbon atoms. Suitable polynitroaromatics are for example 2,4,6-trinitrotoluene, polynitroxylenes, such as 2,4,6-trinitro-m-xylene or 4,5,6-trinitro-m-xylene.

Preferred polynitroaromatics are 2,4,6-trinitrotoluene, 2,4,6-trinitro-m-xylene or 4,5,6-trinitro-m-xylene, with 2,4,6-trinitrotoluene being particularly preferred.

Mixtures of the recited mononitroaromatics, dinitroaromatics and polynitroaromatics are also suitable in accordance with the invention.

It is preferable when the nitro compounds are nitroaromatics, preferably dinitroaromatics, particularly preferably dinitrobenzene, halogenated dinitrobenzenes and dinitrotoluenes and very particularly preferably dinitrotoluene.

In a very particularly preferred embodiment 2,4-dinitrotoluene or 2,6-dinitrotoluene is employed. Industrial mixtures comprising 2,4-dinitrotoluene and 2,6-dinitrotoluene are also suitable, wherein these mixtures preferably comprise up to 35 wt % of 2,6-dinitrotoluene with proportions of preferably 1 to 5 wt %, by preference 1 to 4 wt %, of vicinal dinitrotoluene and preferably 0.5 to 1.5 wt % of 2,5- and 3,5-dinitrotoluene based on the overall mixture.

Mixtures of the recited nitro alcohols and nitroaromatics are also suitable in accordance with the invention.

The recited nitro alcohols and nitroaromatics are commercially available.

The nitro alcohols and nitroaromatics used may furthermore be obtained by chemical synthesis, such as dinitrotoluenes may be obtained by nitration of toluene for example. The thus formed reaction product usually comprises not only the desired nitro compound but also numerous impurities. For example nitrating acid comprising nitric acid, sulfuric acid and nitrogen oxides may be present in this reaction product. Degradation products, such as dinitrogen monoxide, hydrocyanic acid, carbon monoxide or mixtures thereof for example, may also be present as impurities. Oxidation products, for example from undesired side reactions of the nitroaromatics, may likewise be present, for example aromatic carboxylic acids, such as nitrobenzoic acids, for example mononitrobenzoic acid, dinitrobenzoic acid or the degradation products thereof or mixtures thereof.

Further impurities may be present in the form of high boilers, such as nitrocresol, for example mononitrocresol, dinitrocresol or trinitrocresol and nitrophenol, for example dinitrophenol or trinitrophenol.

A purification of the thus obtained nitro compounds is thus generally necessary in order for them to be suitable as reactants for subsequent processes, for example the hydrogenation to the corresponding amines. Processes for the synthesis of nitro compounds and the further purification thereof are generally known to one skilled in the art or are described in US 2014/0039227 A1 for dinitrotoluene for example.

The purification is generally effected in a multistage washing process comprising at least three washing steps: a washing step for removal of the acids, a washing step in the presence of a base for removing weak acids and a neutral washing step for removing remaining alkaline substances.

The resulting washing solutions may comprise nitrocresols or nitroaromatics for example which may be removed for example by precipitation through acidification, by treatment with activated carbon, via strongly basic exchange columns, by extraction using toluene or the aromatic to be nitrated, by oxidation using nitric acid and subsequent thermal decomposition, by decomposition using hydrogen peroxide or ozone or by thermolysis of the nitroaromatics.

After removal of nitrating acid and any nitrocresols and/or nitrobenzoic acids present the purification of the nitroaromatics may also be effected in two washing steps as described for dinitrotoluene in US 2014/0039227 A1. In a first washing step comprising at least one extraction step the crude mixture may be washed with a first washing acid comprising nitric acid, nitrogen oxides and sulfuric acid. The washing solution discharged in the extraction generally has a total content of acid of 20 to 40 wt % based on the total weight of this washing solution and comprises for example nitric acid, nitrogen oxides, such as nitrous acid, and sulfuric acid.

The thus remaining mixture comprising the desired nitro compound is treated in at least one further extraction step for example in a second washing step with a second washing acid. In this extraction step the discharged washing solution generally has a pH of ≤4. A mixture comprising the desired nitro compound which may in principle be free from nitric acid, sulfuric acid and nitrogen oxides is typically obtained. The thus obtained purified nitro compound may generally be used for hydrogenation to the corresponding amine.

The nitro compound obtained from the above-recited purification process or the nitro compound used for hydrogenation generally has a residual acid content of 300 ppm, such as sulfuric acid for example, and a pH of 2 to 4. The nitro compound, for example dinitrotoluene, generally comprises ≤800 ppm of nitrocresols or nitrophenols or mixtures thereof, ≤600 ppm of nitrobenzoic acid, for example mononitrobenzoic acid or dinitrobenzoic acid or mixtures thereof, and a residual content of ≤300 ppm, preferably ≤200 ppm and particularly preferably ≤100 ppm of nitric acid or nitrous acid or mixtures thereof, ≤50 ppm, preferably ≤10 ppm and particularly preferably ≤1 ppm of hydrocyanic acid, ≤200 ppm, preferably ≤50 ppm and particularly preferably ≤25 ppm of dinitrogen oxide, ≤400 ppm, preferably ≤200 ppm and particularly preferably ≤50 ppm of nitrogen monoxide and ≤3 ppm of sulfate.

In a preferred embodiment in addition to the nitro compound for hydrogenation the reaction mixture comprises at least one high boiler from the group consisting of nitrocresols and nitrophenols. In a particularly preferred embodiment in addition to the nitro compound for hydrogenation the reaction mixture comprises at least one high boiler from the group consisting of dinitrocresols, trinitrocresols and nitrophenols.

In another preferred embodiment in addition to the nitro compound for hydrogenation the reaction mixture comprises no high boilers from the group consisting of nitrocresols and nitrophenols. In another particularly preferred embodiment in addition to the nitro compound for hydrogenation the reaction mixture comprises no high boilers from the group consisting of dinitrocresols, trinitrocresols and nitrophenols.

In a further preferred embodiment in addition to the nitro compound for hydrogenation the reaction mixture comprises at least one compound from the group consisting of nitric acid, sulfuric acid, nitrogen oxides, dinitrogen monoxide, hydrocyanic acid, carbon monoxide and nitrobenzois acid or degradation products thereof.

For the hydrogenation process according to the invention the nitro compound may be employed in pure form, as a mixture with the corresponding mono-, di- or polyamine, as a mixture with the corresponding mono-, di- or polyamine and water, as a mixture with the corresponding mono-, di- or polyamine, water and an alcoholic solvent or as a mixture with the corresponding di- or polyamine, water, an alcoholic solvent and a catalyst-reactivating addition, wherein mixtures of two or more of the abovementioned nitro compounds, of the corresponding amine compounds, of the alcoholic solvent and of the catalyst-reactivating addition may also be employed in each case.

Preferably employed catalyst-reactivating additions are aprotic solvents, in particular dimethyl-formamide (DMF) dioxane or tetrahydrofuran (THF) or a mixture of two or more thereof.

Suitable alcoholic solvents are generally lower aliphatic alcohols having 1 to 6 carbon atoms. Preference is given to using methanol, ethanol or propanol, individually or in a mixture of two or more thereof. Particular preference is given to using ethanol.

Provided that an abovedescribed mixture is employed the weight ratio of an amine compound to water is preferably in the range from 10:1 to 1:10, preferably in the range from 8:1 to 1:5 and particularly preferably in the range from 4:1 to 1:1 and the weight ratio of the amine/water mixture to at least one alcoholic solvent is preferably 1000:1 to 1:1, preferably 500:1 to 2.5:1 and particularly preferably 50:1 to 5:1.

The amount of the employed alcoholic solvent and of the catalyst-reactivating additions is not restricted in any particular way in the context of the process according to the invention and may be chosen freely as required.

The process according to the invention for hydrogenation of nitro compounds to the corresponding amines may additionally be performed in the absence of solvents. In this procedure the workup of the reaction mixture after the hydrogenation is simplified and side reactions with the solvent are moreover completely inhibited.

The purified nitro compound may generally be used for hydrogenation to the corresponding amines. However, the remaining impurities and the byproducts formed during the hydrogenation, for example high boilers, may contribute to the aging of the catalyst.

Ammonia

The added amount of ammonia is preferably at least 200 mmol per kg of added nitro compound, in particular at least 400 mmol, particularly preferably at least 1000 mmol, very particularly preferably at least 1200 mmol.

The added amount of ammonia is preferably at most 3000 mmol per kg of added nitro compound, in particular at most 2500 mmol, particularly preferably at most 2000 mmol, very particularly preferably at most 1800 mmol.

Ammonia is preferably added in an amount of 200 to 3000 mmol per kg of added nitro compound, in particular of 400 to 2500 mmol, particularly preferably of 1000 to 2000 mmol, very particularly preferably of 1200 to 1800 mmol.

In a first embodiment the ammonia may be added in the abovementioned preferred amounts in the form of liquid ammonia.

In a second embodiment the ammonia may be added in the abovementioned preferred amounts in the form of an aqueous solution. The amount of ammonia based on the total weight of the aqueous ammonia solution is preferably at least 1% by weight, in particular at least 5% by weight, particularly preferably at least 10% by weight, very particularly preferably at least 20% by weight.

The preferred type of addition of ammonia is more particularly elucidated hereinbelow in the context of the performance of the process.

Catalyst

The supported catalyst is to be understood as meaning a catalyst in which an active component is disposed on an inactive component (the support material), in particular distributed over the support material. The active component is the catalytically active component.

Suitable supported catalysts for a process for continuous hydrogenation of nitro compounds to the corresponding amines in the liquid phase are generally known to one skilled in the art or are described in EP 1 678 118 B1, DE 10 2005 041 532 A1, WO 2008/138784 A1 and U.S. Pat. No. 6,140,539 for example.

Suitable active components for a catalyst for hydrogenation of nitroaromatics to the corresponding amines are generally known to one skilled in the art or are described in EP 1 678 118 B1, DE 10 2005 041 532 A1, WO 2008/138784 A1, EP 1161297 A1, EP 1165231 A1 and U.S. Pat. No. 6,140,539 for example.

The supported catalyst generally comprises at least one element from groups 7 to 12 of the periodic table of the elements as the active component. Elements from groups 7 to 12 of the periodic table of the elements suitable as the active component of the supported catalyst are for example iron, cobalt, nickel, ruthenium, rhodium, palladium, silver, osmium, iridium, platinum, gold, copper, rhenium, zinc and/or manganese.

The active component of the supported catalyst preferably comprises at least one element from groups 7 to 12 of the periodic table of the elements, particularly preferably at least one element from the group consisting of nickel, platinum, palladium, iron and cobalt, very particularly preferably at least one element from the group consisting of nickel, platinum, palladium and cobalt and especially preferably at least nickel.

The catalyst generally comprises 0 to 10 wt %, preferably 1 to 5 wt %, of noble metal based on the total weight of the catalyst.

The active component of the catalyst may optionally further comprise chromium in addition to the at least one element from the groups 7 to 12 of the periodic table of the elements.

In order to suppress side reactions it is preferable to conduct the process such that the catalyst is run at its loading limit. This may be controlled through the amount of metered-in nitro compound, the amount of catalyst in the reaction mixture, the temperature or the pressure for example. The loading limit of the catalyst in the context of the invention is to be understood as meaning the amount of hydrogenatable nitrogen- and oxygen-comprising groups that can be hydrogenated by the catalyst at given pressure and temperature conditions. The nitrogen- and oxygen-comprising groups may be nitroso groups and nitrosamine groups as well as nitro groups.

In a first embodiment nickel may be used as the active component on a support as described in U.S. Pat. No. 6,140,539, wherein the catalyst is stabilized and the nickel crystallites have a bimodal nickel crystallite size distribution, a nickel content of 60 to 80 wt % based on the total mass of the catalyst and a degree of reduction of at least 70%.

Determination of the degree of reduction is generally effected during a one-hour postreduction of the stabilized catalyst at 100° C.

The two maxima of the bimodal nickel crystallite size distribution are generally at 30 to 80 Ångströms and 81 to 150 Ångströms. The proportion of nickel in the region of the maximum of 30 to 80 Ångströms is preferably from ≥40 to <100 wt % based on the total mass of the catalyst.

Suitable support materials for this first embodiment are for example oxides and oxide mixtures of zirconium, hafnium or silicon. The support preferably comprises $ZrO_2$, $ZrO_2.HfO_2$, $SiO_2.ZrO_2$ or $SiO_2.ZrO_2HfO_2$ or mixtures comprising at least two of these substances. The support particularly preferably consists of these substances.

The $SiO_2$ content is preferably 0 to 20 wt % based on the total mass of the catalyst.

The $ZrO_2$ content is preferably 0 to 40 wt % based on the total mass of the catalyst. The $HfO_2$ content is preferably 0 to 4 wt % based on the total mass of the catalyst.

Processes for producing such a catalyst are generally known to one skilled in the art or are described in U.S. Pat. No. 6,140,539 for example.

It is preferable when the active component of the supported catalyst comprises nickel in the form of nickel crystallites having a bimodal nickel crystallite size distribution and has a nickel content of 60 to 80 wt % based on the total mass of the catalyst and a degree of reduction of at least 70%.

In a second embodiment the process according to the invention for continuous hydrogenation of nitro compounds to the corresponding amines uses a supported catalyst whose active component comprises a mixture of nickel and platinum and optionally at least one additional metal, as described in EP 1678118 B1 or DE 10 2005 041 532 A1 for example.

Active components of this catalyst are generally applied to the support material in the form of mixtures. Suitable mixtures comprise nickel and platinum in an atom ratio of nickel to platinum of preferably between 30:70 and 70:30, by preference between 40:60 and 60:40 and particularly preferably between 45:55 and 55:45. Mixtures of nickel and platinum having a different atom ratio are likewise usable but often result in low product yields.

It is preferable when at least one additional metal is added to the mixture comprising nickel and platinum. Metals suitable as the additional metal are generally known to one skilled in the art or are described in DE 10 2005 041 532 A1 for example. The additional metal is preferably at least one metal from the group consisting of copper, cobalt, iron, zinc, manganese and chromium, particularly preferably at least one metal from the group consisting of copper, cobalt, iron and zinc.

The metal particles are generally polycrystalline. The characterization thereof is generally known to one skilled in the art or is described in DE 10 2005 041 532 A1 for example.

The constitution of, and processes for the characterization of, the supported catalyst whose active material may be a mixture of nickel and platinum and optionally at least one additional metal are generally known to one skilled in the art or are described in EP 1678118 B1 or DE 10 2005 041 532 A1.

The hydrogenation catalyst based on nickel and platinum and at least one additional metal and used in the process according to the invention generally comprises
1 to 5 wt % of platinum,
0.3 to 1.5 wt % of nickel,
0.05 to 1.5 wt % of the at least one additional metal and
94.65 to 97.45 wt % of support material
based on the total weight of the catalyst.

The hydrogenation catalyst based on nickel and platinum and at least one additional metal and used in the process according to the invention is particularly preferably composed of
1 to 5 wt % of platinum,
0.3 to 1.5 wt % of nickel,
0.05 to 1.5 wt % of the at least one additional metal and
94.65 to 97.45 wt % of support material
based on the total weight of the catalyst.

The content of non-noble metals is generally 0 to 1.6 wt %, preferably 0.1 to 0.9 wt %, based on the total weight of the catalyst.

The materials suitable as supports for the catalysts of this second embodiment are generally known to one skilled in the art or are described in EP 1678118 B1 or DE 10 2005 041 532 A1 for example. Activated carbon, carbon black, graphite or metal oxides, preferably hydrothermally stable metal oxides, for example $ZrO_2$ and/or $TiO_2$, or oxides of aluminum, such as $Al_2O_3$, or of silicon or other materials are generally employed.

It is preferable when graphite is used as the support, HSAG (high surface area graphite) having a surface area of 50 to 300 $m^2/g$ being particularly preferable in this case.

It is particularly preferable to use activated carbon as the support. A very particularly preferred embodiment is the use of physically or chemically activated carbon or carbon blacks, such as acetylene black, as the support.

Processes for producing the supported catalyst whose active material is a mixture of nickel and platinum and optionally at least one additional metal are generally known to one skilled in the art or are described in EP 1678118 B1 or DE 10 2005 041 532 A1.

The catalyst based on a mixture of nickel and platinum and optionally at least one additional metal and used in the process according to the invention is preferably employed in an amount of 0.01 to 10 wt %, preferably 0.1 to 5 wt % and particularly preferably 0.2 to 2 wt % based on the total weight of the reaction mixture.

The active component of the supported catalyst preferably comprises a mixture of nickel and platinum and optionally at least one additional metal.

The additional metal is preferably at least one metal from the group consisting of copper, cobalt, iron, zinc, manganese and chromium, particularly preferably at least one metal from the group consisting of copper, cobalt, iron and zinc.

In a third embodiment of the process according to the invention catalysts may be employed which comprise as the active component a mixture of nickel, palladium and an additional element selected from the group consisting of cobalt, iron, vanadium, manganese, chromium, platinum, iridium, gold, bismuth, molybdenum, selenium, tellurium, tin and antimony on a support. This process may in particular be used for producing tolylenediamine by hydrogenation of dinitrotoluene. The performance of a hydrogenation of nitro compounds to the corresponding amines using this catalyst is generally known to one skilled in the art or is described in WO 2008/138784 A1 for example.

The additional element is preferably selected from the group consisting of cobalt, iron, vanadium, bismuth and tin.

As the support for the catalyst of this third embodiment the materials known and customary therefor may generally be employed. It is preferable to employ activated carbon, carbon black, graphite or metal oxides, preferably hydrothermally stable metal oxides such as $ZrO_2$, $TiO_2$, $Al_2O_3$. Preferred graphites are HSAG (high surface area graphites) having a surface area of 50 to 300 $m^2/g$. Particular preference is given to activated carbons, in particular physically or chemically activated carbons, or carbon blacks, such as acetylene black.

In a further embodiment of the process according to the invention the active component of the catalyst is not Raney nickel.

The catalyst used in the process according to the invention is generally employed in an amount of 0.01 to 10 wt %, preferably 0.1 to 5 wt % and particularly preferably 0.2 to 2 wt % based on the total weight of the reaction mixture.

The catalyst is typically introduced into the reactor in a reduced and passivated state. The reduced and passivated state in the context of the invention is to be understood as meaning that the catalyst is activated after production but that the active centers are then passivated for safety reasons for example by passing oxygen or carbon dioxide over them. The installation and stabilization of the catalyst under an inert atmosphere or in a non-highly-flammable solvent, for example in water or a mixture of toluenediamine and water or higher alcohols, for example butanol or ethylene glycol, are also suitable.

Procedure

The reactors and modes of reactor operation suitable for the process according to the invention are generally known to one skilled in the art or are described in DE10 2005 041 532 A1, DE 10 2008 063 308 B4, WO 2000/035852 A1 or WO 2014/108351 A1 for example.

The process parameters, such as pressure and temperature, to be used for the process according to the invention are likewise generally known to one skilled in the art or are described in DE 10 2005 041 532 A1, DE 10 2008 063 308 B4, WO 2000/035852 A1 oder WO 2014/108351 A1 for example.

Suitable reactors are for example stirred tanks or tube bundle reactors or loop reactors, such as jet loop reactors, so-called loop venturi reactors or loop reactors with internal flow reversal as described in WO 2000/035852 A1, DE10 2005 041 532 A1, DE 10 2008 063 308 B4 or WO 2014/108351 A1. It is preferable to employ a loop reactor for the process according to the invention.

The nitro compounds are generally added at a rate that is both tailored to the catalyst activity and achieves a sufficient mixing with the flow in the loop reactor, the so-called circulation stream. The catalyst activity is generally adjusted, by addition of sufficient catalyst amounts, such that the feed stream of the nitro compounds is determined by the circulation stream so that local overconcentrations of nitro compounds (for example greater than 10 000 ppm) are avoided. In the case of a reactor with flow reversal an internal circulation flow which is greater than the circulation stream may form for example through the impact of the introduced reaction mixture onto the reactor floor or through internals. If the nitro compound is fed into the internal circulation flow in this case, the feed stream of said compound is determined by the size of the internal circulation flow in order to avoid local overconcentrations for a given conversion in the internal circulation loop.

In a preferred embodiment, a second feed point through which additional components, especially the ammonia added in accordance with the invention, are introduced into the process is located, viewed in the direction of flow, downstream of the first feed point for the nitro compound.

The ammonia may generally be introduced into the reactor and hence into the reaction chamber at any desired location. Ammonia is preferably not added together with the nitro compounds supplied into the reactor but rather separately therefrom. The addition is thus preferably carried out immediately downstream of the addition of the nitro compound. This ensures good and rapid commixing in the entire reaction region.

The weight hourly space velocity employed in the process according to the invention is preferably 5 to 100 kg (nitro compound)/kg (catalyst)/h, by preference 10 to 50 kg (nitro compound)/kg (catalyst)/h and particularly preferably 15 to 35 kg (nitro compound)/kg (catalyst)/h.

Suitable hydrogenating gas mixtures for continuous hydrogenation of nitroaromatics to the corresponding amines are generally known to one skilled in the art or are described in EP 1678 118 B1 for example.

Hydrogenating gas mixtures that may be employed are generally gases which comprise free hydrogen and which do not comprise damaging amounts of catalyst poisons, for example carbon monoxide. Suitable hydrogenating gas mixtures are reformer offgases or mixtures of hydrogen with nitrogen and/or carbon dioxide. It is preferable when hydrogen having a low inert gas content is employed as the hydrogenating gas mixture.

The supply of the hydrogenating gas mixtures is generally effected as a function of the hydrogen consumption by the reaction by preferably keeping the pressure prevailing in the reactor apparatus constant. Continuous removal of a portion of the gas phase allows an accumulation of inert fractions in the hydrogenating gas mixture or of inert gaseous reaction products to be avoided.

In a first embodiment the process according to the invention may be performed at temperatures of 80° C. to 200° C., preferably 110° C. to 190° C., particularly preferably 150° C. to 190° C., as described in WO 2014/108351 A1 or DE 10 2008 063 308 B4. The process of this first embodiment is generally performed at pressures of 10 to 50 bar, preferably 15 to 35 bar. The heat of reaction thus formed may be utilized to obtain steam at an overpressure of at least 4 bar using heat transferors. The parameters necessary for performing this process are generally known to one skilled in the art or are described in WO 2014/108351 A1 or DE 10 2008 063 308 B4 for example.

The process according to the invention for hydrogenation of nitro compounds to amines, for example the hydrogenation of dinitrotoluene to tolylenediamine derivatives, is preferably performed in a vertically elongated reactor, as described in WO 2014/108351 A1, which comprises at least one mixing chamber, wherein the mixing chamber or the mixing chambers are each connected at their lower end to a diffuser.

Heat transferors and cooling media suitable for performing this process are likewise generally known to one skilled in the art or are described in WO 2014/108351 A1 or DE 10 2008 063 308 B4 for example.

In a second embodiment the process according to the invention may be performed at temperatures of preferably 80° C. to 250° C., by preference 100° C. to 200° C. and particularly preferably 120° C. to 150° C. as described in WO 00/35852 A1 or DE 10 2005 041 532 A1. The process in this second embodiment is generally performed at pressures of preferably 5 to 100 bar, by preference 10 to 40 bar and particularly preferably 20 to 25 bar.

Suitable reactors are generally known to one skilled in the art or are described in WO 00/35852 A1 or DE 10 2005 041 532 A1 for example. Stirred tanks or loop reactors, such as jet loop reactors, so-called loop venturi reactors or loop reactors with internal flow reversal may generally be employed.

The amines formed in the hydrogenation may generally be withdrawn from the process continuously or discontinuously. It is preferable when the amines formed in the hydrogenation are continuously withdrawn from the process.

The withdrawal of the amines formed in the hydrogenation may be effected at any desired location. It is preferable when the withdrawal is effected from the external circulation flow upstream of the introduction of the nitro compound. Since under the recited conditions in the internal circulation flow the hydrogenation of the nitro compound is generally practically quantitative, the external circulation flow upstream of the introduction of the nitro compound comprises essentially the corresponding pure amine, water, optionally solvent and catalyst. The amine is generally removed from the withdrawn stream and sent to the purification. The catalyst and optionally water may be sent back to the external circulation flow.

The catalyst is preferably suspended in the reaction medium. The removal of the reaction product from the catalyst is generally effected by means of membrane filtration. The membrane utilized therefor may preferably be installed in the outer recirculating flow or for example in the continuously stirred tank. Alternatively the catalyst may also be retained by sedimentation in a settler installed in the outer recirculating flow or for example in the continuously stirred tank.

The membrane filtration is preferably performed at a pressure on the suspension side of 5 to 50 bar, preferably 20 to 35 bar, a pressure difference between the suspension side and the permeate side of 0.3 bar to 5 bar and a flow velocity on the suspension side of 1 to 6 m/s. Suspension side in the context of the invention is to be understood as meaning the side of the membrane filter on which the catalyst-comprising mixture is located. Permeate side in the context of the invention is to be understood as meaning the side of the membrane filter on which the catalyst-free mixture is located.

The membrane filtration may be performed continuously or discontinuously.

In continuous mode generally at least a substream of the reaction mixture is constantly run through a membrane filter. In a preferred embodiment of the process according to the invention it is preferable to arrange the membrane filter in the external circuit of a recirculating reactor.

In the discontinuous mode of the filtration the discharge reaction mixture is generally passed through a connectable purification stage consisting of at least one membrane filter and a dedicated circulation pump. In another configuration of the discontinuous filtration the reaction mixture is run through a membrane filter following the reaction.

The filter membranes employed for the process may, for example, be made of ceramic (e.g. α-Al$_2$O$_3$) or stainless steel (e.g. 1.4404) and independently of the particle size of the employed catalyst preferably have a number-weighted average pore diameter in the range from 10 nm to 20 micrometers, particularly preferably in the range from 20 nm to 10 micrometers and very particularly preferably from 50 nm to 1 micrometer.

Suitable embodiments of a membrane filtration, in particular cross-flow filtration, are known to one skilled in the art and are described for example in WO2010/125025 or WO 2003/066571, the content of which is hereby incorporated into this application by reference.

After removal of the catalyst the amines formed are generally subjected to further purification. Processes for purification of the amines produced in accordance with the invention are generally known to one skilled in the art or are described in WO 2000/035852 A1 for example.

Suitable processes for purification of the amines formed are for example distillation or extraction.

EXAMPLES

The following experiment was performed in a Miniplant test plant. This consisted of a loop reactor set up which in one part (5.6 L) has an internal circulation flow powered by a motive jet (circulation stream consisting of product and catalyst) and in another part is configured as a tubular reactor (4.4 L). The overall set up was thermostated with thermal oil to remove generated heat. DNT was mixed in close to the motive jet and hydrogen was metered into the gas space above the internal circulation flow under pressure control. Product formed was withdrawn through a catalyst-retaining membrane so that the liquid level in the reactor part with the internal circulation flow remained constant. A fixed amount of gas was discharged above the gas space to prevent unlimited accumulation of gaseous products or impurities.

The reactor was charged with 112 g (dry weight) of 3% Pt-1% Ni/C catalyst suspended in water and operated at 185° C., 25 bar overpressure, with a circulation stream of 500 kg/h and a DNT metering rate of 2 kg/h. This resulted in a WHSV of 17.9 kg(DNT)/kg(cat)/h.

The addition of ammonia was effected by supplying a continuous volume flow of an aqueous solution into the reactor. The introduction was effected through a tube fed through at the reactor top. The solution dripped into the internal circulation flow of the reactor at the edge of the push-in tube, i.e. at a point removed from the DNT feed point. The ammonia concentrations described in Table 1 were established by variation of the volume flow and the concentration of the aqueous ammonia solution. Once a steady-state has been established a plurality of samples were taken and analyzed by gas chromatography.

After a running-in period of 250 hours and significant catalyst aging, ammonia was added and the TDA yield increased gradually according to Table 1.

TABLE 1

| Mmol(NH3)/kg(DNT) | Concentration of added NH$_3$ in water | TDA selectivity |
|---|---|---|
| 0 | | 97.8 |
| 13 | 2% by weight | 97.8 |
| 199 | 10% by weight | 98.2 |
| 397 | 10% by weight | 98.7 |
| 993 | 25% by weight | 98.9 |
| 1322 | 25% by weight | 99.1 |
| 1656 | 25% by weight | 99.2 |
| 1918 | 25% by weight | 99.0 |

The invention claimed is:

1. A process for continuous hydrogenation of a nitro compound to a corresponding amine, the process comprising:
    hydrogenating the nitro compound in a liquid reaction mixture comprising the nitro compound in a reaction chamber in the presence of a supported catalyst which comprises as an active component at least one element selected from groups 7 to 12 of the periodic table of the elements, wherein ammonia is added to the reaction chamber during the hydrogenation, wherein the amount of ammonia added is at least 200 mmol and is at most 3000 mmol, per kg of added nitro compound, and wherein in addition to the nitro compound for hydrogenation the reaction mixture comprises at least one high boiler selected from the group consisting of dinitrocresols, trinitrocresols and nitrophenols.

2. The process according to claim 1, wherein the active component of the catalyst comprises at least one element selected from the group consisting of nickel, platinum, palladium, iron and cobalt.

3. The process according to claim 1, wherein the active component of the catalyst comprises chromium.

4. The process according to claim 1, wherein the active component of the supported catalyst comprises nickel in the form of nickel crystallites having a bimodal nickel crystallite size distribution and has a nickel content of 60 to 80 wt % based on the total mass of the catalyst and a degree of reduction of at least 70%.

5. The process according to claim 1, wherein the active component of the supported catalyst comprises a mixture of nickel and platinum in an atom ratio of nickel to platinum of between 30:70 and 70:30 and optionally one or more additional metals.

6. The process according to claim 5, wherein the catalyst based on nickel and platinum and at least one additional metal and used in the process comprises:
    1 to 5 wt % of platinum,
    0.3 to 1.5 wt % of nickel,
    0.05 to 1.5 wt % of the at least one additional metal, and
    94.65 to 97.45 wt % of support material
    based on the total weight of the catalyst.

7. The process according to claim 5, wherein the additional metal is at least one metal selected from the group consisting of copper, cobalt, iron, zinc, manganese and chromium.

8. The process according to claim 7, wherein the amount of ammonia added is at least 1000 mmol, per kg of added nitro compound.

9. The process according to claim 1, wherein the added amount of ammonia is at most 2000 mmol, per kg of added nitro compound.

10. The process according to claim 1, wherein the ammonia is added in liquid form.

11. The process according to claim 1, wherein the ammonia is added as an aqueous solution.

12. The process according to claim 1, wherein the nitro compound for hydrogenation is a nitroaromatic.

13. The process according claim 1, wherein in addition to the nitro compound for hydrogenation the reaction mixture comprises no high boilers selected from the group consisting of dinitrocresols, trinitrocresols and nitrophenols.

14. The process according to claim 1, wherein in addition to the nitro compound for hydrogenation the reaction mixture comprises at least one compound selected from the group consisting of nitric acid, sulfuric acid, nitrogen oxides, dinitrogen monoxide, hydrocyanic acid, carbon monoxide and nitrobenzoic acid or degradation products thereof.

15. The process according to claim 1, wherein the hydrogenation is performed at a temperature of 80° C. to 250° C.

16. The process according to claim 1, wherein the hydrogenation is performed in the absence of solvents.

* * * * *